US011521733B2

(12) United States Patent
Song et al.

(10) Patent No.: US 11,521,733 B2
(45) Date of Patent: Dec. 6, 2022

(54) EXERCISE ASSISTANT DEVICE AND EXERCISE ASSISTANT METHOD

(71) Applicant: Codevision Inc., Seoul (KR)

(72) Inventors: Eung Yeol Song, Cheonan-si (KR); Sung Ju Park, Seoul (KR)

(73) Assignee: CODEVISION INC., Seoul (KR)

( * ) Notice: Subject to any disclaimer, the term of this patent is extended or adjusted under 35 U.S.C. 154(b) by 274 days.

(21) Appl. No.: 16/905,133

(22) Filed: Jun. 18, 2020

(65) Prior Publication Data
US 2020/0402638 A1 Dec. 24, 2020

(30) Foreign Application Priority Data

Jun. 20, 2019 (KR) .......................... 10-2019-0073310

(51) Int. Cl.
*G16H 20/30* (2018.01)
*G16H 10/60* (2018.01)
(Continued)

(52) U.S. Cl.
CPC ............ *G16H 20/30* (2018.01); *A61B 5/1114* (2013.01); *A63B 24/0087* (2013.01); *G06N 3/02* (2013.01);
(Continued)

(58) Field of Classification Search
USPC ........................................................ 482/51
See application file for complete search history.

(56) References Cited

U.S. PATENT DOCUMENTS 10,065,074 B1* 9/2018 Hoang ................. G09B 19/003
11,259,743 B2* 3/2022 Obma .................. A61B 5/4528
(Continued)

FOREIGN PATENT DOCUMENTS

JP 2017-136142 A 8/2017
KR 10-2016-0133676 A 11/2016
(Continued)

OTHER PUBLICATIONS

Korean Office Action dated Oct. 15, 2020 for corresponding Korean Application No. 10-2019-0073310 and English translation.
(Continued)

*Primary Examiner* — Pierre E Elisca
(74) *Attorney, Agent, or Firm* — Pearne & Gordon LLP

(57) ABSTRACT

There is provided a device for assisting exercise, comprising a video providing unit configured to provide a first video data including a first exercise movement, a data obtaining unit configured to obtain a second video data based on an input relating to the first video data, a joint information extracting unit configured to extract a first joint information obtained by detecting plural skeletons from the second video data, an analyzing unit configured to obtain an analysis information based on a similarity determined by comparing the first joint information with a second joint information of the first video data and a recommendation unit configured to obtain recommendation information for recommending an exercise movement to a user based on at least one of the first video data, the second video data and the analysis information from a database including plural exercise movements may be provided according to an embodiment.

2 Claims, 15 Drawing Sheets

(51) Int. Cl.
  *A63B 24/00* (2006.01)
  *G06N 3/02* (2006.01)
  *A61B 5/11* (2006.01)
  *G06V 20/40* (2022.01)
  *G06V 40/20* (2022.01)

(52) U.S. Cl.
  CPC .............. *G06V 20/46* (2022.01); *G06V 40/23* (2022.01); *G16H 10/60* (2018.01)

(56) References Cited

U.S. PATENT DOCUMENTS

| | | | |
|---|---|---|---|
| 2016/0335485 | A1 | 11/2016 | Kim |
| 2017/0221379 | A1 | 8/2017 | Onda |
| 2019/0362506 | A1* | 11/2019 | Leroyer .................. G06V 20/40 |
| 2020/0015712 | A1* | 1/2020 | Hayashida ......... G08B 21/0446 |
| 2021/0307650 | A1* | 10/2021 | Barr ..................... A61B 5/0022 |

FOREIGN PATENT DOCUMENTS

| | | |
|---|---|---|
| KR | 10-1936692 B1 | 1/2019 |
| KR | 10-1959079 B1 | 3/2019 |
| KR | 10-1980378 B1 | 8/2019 |

OTHER PUBLICATIONS

Korean Office Action dated Apr. 21, 2021 for corresponding Korean Application No. 10-2019-0073310 and English translation.
Notice of Allowance dated Dec. 10, 2021 for corresponding Korean Application No. 2019-0073310 and English translation.

* cited by examiner

EXERCISE ASSISTANT DEVICE AND EXERCISE ASSISTANT METHOD

CROSS-REFERENCE TO RELATED APPLICATION

This application claims priority to and the benefit of Korean Patent Application No. 10-2019-0073310, filed on Jun. 20, 2019, the disclosure of which is incorporated herein by reference in its entirety.

BACKGROUND

1. Field of the Invention

Embodiments relate to an exercise assistance device and an exercise assistance method. The present application was supported by the Technology Innovation Program (20006697, Multi sensor based artificial intelligence technology passenger recognition and air clean console for autonomous design companion animal family centered) funded By the Ministry of Trade, Industry & Energy (MOTIE, Korea)

2. Discussion of Related Art

Recently, the importance of an individual's steady health care is increasing day by day. In addition, users can manage health through exercise devices or exercise facilities and utilize exercise programs for this. Also, for personalized health management, users utilize personal training services as exercise programs.

Meanwhile, the development of artificial intelligence in the field of video analysis has been actively conducted along with the recent rapid development of deep learning technology. Also, global companies such as Google and IBM are investing in developing artificial intelligence for analyzing various body video data, such as inputting large-scale data through collaboration with the medical industry, and some companies have succeeded in developing artificial intelligence that outputs excellent video analysis results.

In this regard, for exercise programs with trainers, a need for a user-customized home training service through analysis of user exercise videos using artificial intelligence technology is emerging, considering that schedule management with a trainer is not easy, that there are temporal and spatial restrictions, and that the cost is high.

SUMMARY OF THE INVENTION

The present invention is directed to providing an exercise assistance device and method capable of performing an analysis and recommendation on an exercise video.

The present invention is also directed to providing an exercise assistance device and method capable of performing movement analysis and movement recommendation on an exercise video through an exercise assistance server.

The present invention is also directed to providing an exercise assistance device and method capable of performing a movement analysis on a user's exercise video through the exercise assistance server and recommending and providing an exercise movement suitable for the user.

Technical problems intended to be solved by the invention are not limited to the aforementioned objects, and other technical objects that are not described herein will be clearly understood by those skilled in the art from the following description and the accompanying drawings.

According to an aspect of the present disclosure, there is provided a device for assisting exercise, comprising a video providing unit configured to provide a first video data including a first exercise movement, a data obtaining unit configured to obtain a second video data based on an input relating to the first video data, a joint information extracting unit configured to extract a first joint information obtained by detecting plural skeletons from the second video data, an analyzing unit configured to obtain an analysis information based on a similarity determined by comparing the first joint information with a second joint information of the first video data and a recommendation unit configured to obtain recommendation information for recommending an exercise movement to a user based on at least one of the first video data, the second video data and the analysis information from a database including plural exercise movements.

According to an aspect of the present disclosure, there is provided A method for assisting exercise, the method including providing a video providing a first video data including a first exercise movement, obtaining a second video data including a second exercise movement obtained by responding to an input of the first video data, extracting a fist joint information obtained by detecting plural skeleton from the second video data, providing analysis information based on a similarity determined by comparing the first joint information with the second joint information of the first video data and providing a recommendation information recommends an exercise movement based on at least one of the first video data, the second video data and the analysis information from a data base including plural exercise movements, in order to recommend an appropriate exercise movement to a user.

According to an embodiment, by providing the exercise assistance device and method capable of performing an analysis and recommendation on an exercise video, a user can easily acquire feedback on the exercise video without temporal and spatial restrictions.

According to an embodiment, by providing an exercise assistance device and method capable of performing a movement analysis and a movement recommendation on an exercise video through an exercise assistance server, a user can automatically acquire analysis information and recommendation information with high accuracy through the exercise assistance server.

According to an embodiment, by providing an exercise assistance device and method capable of performing a movement analysis on a user's exercise video through the exercise assistance server and recommending and providing an exercise movement suitable for the user, the user can easily acquire feedback on the exercise movement on the basis of analysis information obtained through the analysis of the exercise video, and the user can acquire an exercise movement recommended on the basis of the analysis information as personalized information.

Advantageous effects of the present disclosure are not limited to those described above, and other unmentioned advantageous effects should be clearly understood by those of ordinary skill in art to which the present disclosure pertains from the present specification and accompanying drawings.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
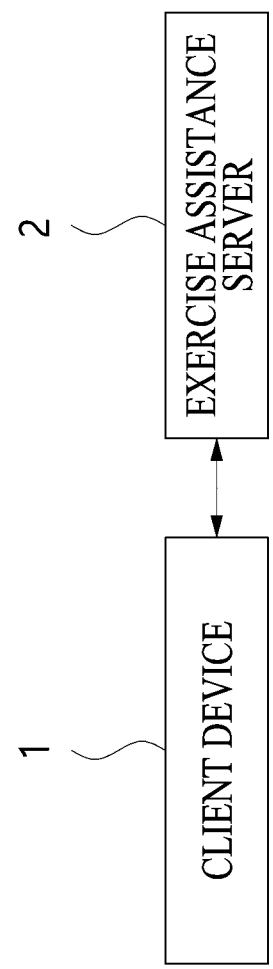
FIG. 1 is a diagram showing an exercise assistance device according to an embodiment.

Hereinafter, embodiments of the present invention will be described in detail with reference to the accompanying drawings. However, it should be noted that the spirit of the present invention is not limited to the embodiments set forth herein and those skilled in the art and understanding the present invention can easily accomplish retrogressive inventions or other embodiments included in the spirit of the present invention by the addition, modification, and removal of elements within the same spirit, but those are construed as being included in the spirit of the present invention.

Further, like reference numerals will be used to designate like elements having similar functions throughout the drawings within the scope of the present invention.

According to an aspect of the present disclosure, there is provided a device for assisting exercise, comprising a video providing unit configured to provide a first video data including a first exercise movement, a data obtaining unit configured to obtain a second video data based on an input relating to the first video data, a joint information extracting unit configured to extract a first joint information obtained by detecting plural skeletons from the second video data, an analyzing unit configured to obtain an analysis information based on a similarity determined by comparing the first joint information with a second joint information of the first video data and a recommendation unit configured to obtain recommendation information for recommending an exercise movement to a user based on at least one of the first video data, the second video data and the analysis information from a database including plural exercise movements may be provided according to an embodiment.

The video providing unit configured to provide the first video data while the second exercise movement is performed.

The first joint information is obtained for each of frames included in the second video data, wherein each of the frames is obtained based on a first interval, wherein the first joint information is obtained by extracting a skeleton corresponding to a body part out of plural skeletons which are included in each of the frames included in the second video data.

The second joint information is obtained for each of frames included in the first video data, wherein each of the frames is obtained based on a second interval, wherein the first joint information is obtained by extracting a skeleton corresponding to a body part out of plural skeletons which are included in each of the frames included in the first video data.

The analyzing unit configured to compare the first joint information with the second joint information, wherein the first joint information and the second joint information are normalized such that the first interval and the second interval correspond to each other.

The analyzing unit configured to obtain an analysis information calculated based on a following equation:

$$\text{Similarity} = \left(100 - \frac{|\theta - \theta^t|}{|\theta^t|} * 100\right)(\%)$$

wherein, $$\theta = \cos^{-1}\left(\frac{A \cdot B}{|A||B|}\right),$$

A is a vector value of the first joint information, B is a vector value of the second joint information, and $\theta^t$ is a predetermined threshold value.

When a similarity included in the analysis information is greater than or equal to a predetermined value, the recommendation unit increases at least one of exercise intensity, number of performance, and performance velocity per for the first video data, or recommends an exercise movement which has a higher level of difficulty than the first video data.

When a similarity included in the analysis information is smaller than or equal to a predetermined value, the recommendation unit decreases at least one of exercise intensity, number of performance, and performance velocity for the first video data, or recommends an exercise movement which has a lower level of difficulty than the first video data.

The second exercise movement is based on imitating movements of a user for the first video data.

The analysis information includes at least one of accuracy, number of performances, a movement time, a performance velocity of movement and an ability of each body part.

The performance number of the second exercise movement is measured based on a change of location of the first joint information.

The analysis information includes first analysis information which analyzes a performance ability for plural body parts, wherein the recommendation information includes a required exercise movement to at least a part of the plural body parts based on the first analysis information.

The plural body parts include at least one of an entire body, an upper body, a lower body, an abdominal region and arms.

The recommendation unit recommends an exercise movement based on at least one of the first video data, the second video data, and the analysis information and pre-obtained a first information, wherein the first information is an information which is obtained from a client device related to a user performing the first exercise movement.

The first information includes at least one of gender, age, condition of health, information of BMI, cycle of exercise, amount of exercise and intensity of exercise.

According to an aspect of the present disclosure, there is provided a method for assisting exercise, the method including, providing a video providing a first video data including a first exercise movement obtaining a second video data including a second exercise movement obtained by responding to an input of the first video data, extracting a fist joint information obtained by detecting plural skeleton from the second video data, providing analysis information based on a similarity determined by comparing the first joint information with the second joint information of the first video data and providing a recommendation information recommends an exercise movement based on at least one of the first video data, the second video data and the analysis information from a data base including plural exercise movements, in order to recommend an appropriate exercise movement to a user. According to an aspect of the present disclosure, there is provided a non-transitory computer-readable recording medium having recorded thereon one or more programs comprising commands for executing the method for assisting exercise.

1. Background and Objectives

In this specification, an exercise assistance device and method based on an exercise assistance server will be described. Also, in this specification, an exercise assistance device and method that provide analysis and recommendation information for input data on the basis of an exercise assistance server are described. In detail, in this specification, an exercise assistance device and method that provide analysis and recommendation information for an exercise video which is input by a client device on the basis of an exercise assistance server are described.

Thus, the exercise assistance device and method do not only provide an analysis result for the input exercise video but can also allow exercise record management for the input exercise video to be efficiently performed. In addition, along with the provision of the analysis result for the input exercise video, the exercise assistance device and method may provide a feedback result on the determination of whether a user's posture shown in the exercise video is correct, and thus the user can more easily correct the posture. Also, the exercise assistance device and method provide recommendation information for the input exercise video so that a personalized exercise recommendation can be performed on the basis of the input exercise video, and thus the user can obtain a more efficient exercise effect based on the recommendation information.

An exercise assistance device and an exercise assistance method according to an embodiment of the present disclosure will be described in detail below.

2. Exercise Assistance Device 2.1 Overview

FIG. 1 is a diagram showing an exercise assistance device according to an embodiment. An exercise-assistance-server-based exercise assistance device may include a client device 1 and an exercise assistance server 2. Also, the exercise-assistance-server-based exercise assistance device may perform exercise assistance through communication between the client device 1 and the exercise assistance server 2. Also, the exercise assistance may be performed through a mutual network between the client device 1 and the exercise assistance server 2.

Thus, in the case of the exercise assistance device, when an exercise video is input to the client device 1, an analysis and/or recommendation may be performed by the exercise assistance server 2 without temporal and spatial restrictions. However, the exercise-assistance-server-based exercise assistance device of the present invention is not limited to the following description, and an analysis and/or recommendation may be performed while some elements are added, changed, or deleted in the following description.

Each element of the exercise-assistance-server-based exercise assistance device will be described in detail below.

2.2 Client Device

The client device 1 may be a device for inputting, receiving, transmitting, or storing video data. Also, the client device 1 may be a device which has a communication function and which is connected or connectable to a network and/or the Internet. Also, the client device 1 may be a communication device capable of connecting to a network through a wireless access unit to transmit or receive data, such as a smart device, and may be at least one of a cell phone, a smartphone, a laptop, a tablet, a netbook, and the like.

Also, the client device 1 may be a device for generating video data or receiving generated video data. As an example, the client device 1 may include a capture unit, and may use a video captured by the capture unit 1 as the video data. Also, the client device 1 may use a mobile application (app), and video data to be analyzed among data stored in or captured by the client device 1 may be transmitted to the exercise assistance server 2 through the mobile app, and an analysis and/or recommendation may be performed on the video data.

In particular, the client device 1 may be a capture device or a device including a capture unit. Also, when the client device 1 is a capture device or a device including a capture unit, the client device 1 may assist exercise by transmitting or sending a video directly captured by the client device 1 to the exercise assistance server 2. Also, when the client device 1 is a capture device or a device including a capture unit, the client device 1 may assist exercise by storing a previously captured video and transmitting or sending the stored image and/or video to the exercise assistance server 2 without temporal and spatial restrictions.

The configuration of the client device 1 will be described in detail below.

2.2.1 Configuration

Figure 2:
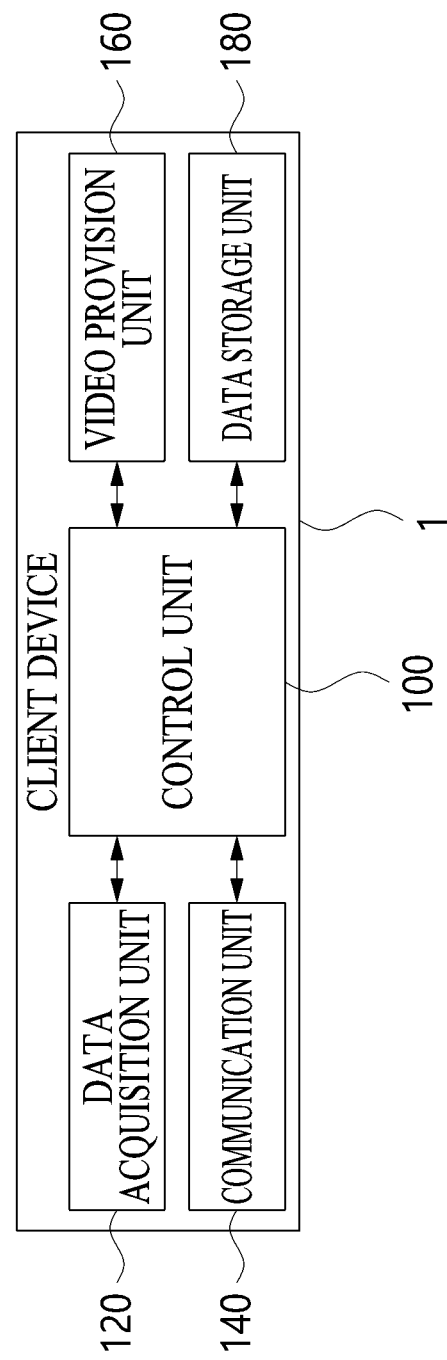
FIG. 2 is a diagram showing a configuration of a client device according to an embodiment.

FIG. 2 is a diagram showing a configuration of the client device 1 according to an embodiment. The client device 1 may include at least one of a control unit 100, a data acquisition unit 120, a communication unit 140, a video provision unit 160, and a data storage unit 180. However, the configuration of the client device 1 is not limited to the above configuration, and some elements may be added or substituted as necessary.

The control unit 100 may control the operation of the client device 1. The control unit 100 may control the operation of at least one of the data acquisition unit 120, the communication unit 140, the video provision unit 160, and the data storage unit 180.

The control unit 100 may include one or more of a central processing unit (CPU), a random access memory (RAM), a graphic processing unit (GPU), one or more microprocessors, and other electronic components capable of processing input data according to a predetermined logic. As an example, the control unit 100 may deploy classification or recommendation process data or the like for exercise assistance between the exercise assistance server 2 and the client device 1, which will be described later, on the RAM and may perform various processes according to a deployed program.

The data acquisition unit 120 may acquire data requested for analysis and/or recommendation for exercise assistance. Also, the data acquisition unit 120 may select and acquire the data requested for analysis and/or recommendation among the data stored in the client device 1. Also, the data acquisition unit 120 may acquire data captured by the capture unit of the client device 1 as the data requested for analysis and/or recommendation.

In particular, the data acquired by the data acquisition unit 120 may be video data. When the data acquired by the data acquisition unit 120 is video data, the data acquisition unit 120 may acquire a selected section or frame of the video data requested for analysis and/or recommendation. The data which is requested for analysis and/or recommendation and which is acquired by the data acquisition unit 120 may have any format among JPG, PNG, DCM(DICOM), BMP, GIF, TIFF, AVI, MP4, WMV, MOV, MKV, TS, TP, FLV, and 3GP.

Also, the data acquisition unit 120 may acquire information regarding a user's gender, age, health status, BMI information, etc. Also, the data acquisition unit 120 may acquire information regarding a user's exercise cycle, exercise amount, exercise intensity, etc.

The communication unit 140 may transmit or send data acquired by the data acquisition unit 120 to the exercise assistance server 2. Also, the communication unit 140 may enable the client device 1 to receive information provided by the exercise assistance server 2. Also, the communication unit 140 may perform not only the transmission of data but also a function of transmitting information associated with the data at the same time or a different time. Also, when the communication unit 140 performs a function for transmission and reception between the client device 1 and the exercise assistance server 2, the transmission and reception function may be performed at the same time or a different time. Also, the communication unit 140 may perform a function of connecting to a network. The communication unit 140 may perform a function of transmitting, to the exercise assistance server 2 through a network, at least one of data and information which are input from the client device 1.

The communication unit 140 may be a device or a component capable of performing at least one of the above-described functions. However, the communication unit 140 is not limited to the above description.

The data storage unit 180 may store data acquired by the data acquisition unit 120, information received from the exercise assistance server 2 by the communication unit 140, data provided by the video provision unit 160, etc. The data storage unit 180 may load the data acquired by the data acquisition unit 120, the information received from the exercise assistance server 2 by the communication unit 140, the data provided by the video provision unit 160, etc., if necessary. In addition, the data storage unit 180 may also store time and/or space (GPS) information regarding the data acquired by the data acquisition unit 120, the information received from the exercise assistance server 2 by the communication unit 140, the data provided by the video provision unit 160, etc.

The video provision unit 160 will be described in detail below.

2.2.2 Video Provision Unit 2.2.2.1 Overview

When the client device 1 acquires data to be requested for analysis and/or recommendation by the exercise assistance server 2, the data acquired from the data acquisition unit 120 needs to be a video suitable for performing an analysis and/or recommendation on a user's exercise movement.

The video provision unit 160 may provide a video for guiding a user to perform capturing on the basis of the video provided from the client device 1 such that the data acquired from the data acquisition unit 120 is suitable for performing analysis and/or recommendation on the user's exercise. When the video provision unit 160 provides a video for guiding the user to perform a predetermined exercise movement, video data including the predetermined exercise movement to be performed by the user may be acquired by the data acquisition unit 120.

Thus, the exercise assistance device may perform an analysis and/or recommendation on a video on the user's exercise performed on the basis of the video provided by the video provision unit 160. Accordingly, the client device 1 can easily provide a guideline of the exercise movement to the user, and the exercise assistance server can easily provide feedback information for the exercise movement to the user.

2.2.2.2 Guide Video

The video provision unit 160 may provide a guide video including a guideline for the data requested for analysis and/or recommendation among the data acquired by the data acquisition unit 120. The guide video may be a video including an exercise movement provided according to the user's selection. Also, the guide video may be a video including an exercise movement provided according to analysis and/or recommendation information provided by the exercise assistance server 2.

The guide video may be a video on a previously captured exercise movement, and the exercise movement may be for at least one body part among a whole body, an upper body, an abdomen part, an arm, and a lower body. Also, when the exercise movement is for the whole body part, the exercise movement may include jumping jacks, high knee walking, wireless jumping rope, and the like. Also, when the exercise movement is for an upper body part, the exercise movement may include dynamic chest stretches, chest presses, clockwise arm rotations, and the like. Also, when the exercise movement is for an abdomen part, the exercise movement may include standing side crunches, crunches, side drops, and the like. Also, when the exercise movement is for an arm part, the exercise movement may include punches, tricep kickbacks, bicep curl pulses, and the like. Also, when the exercise movement is for a lower body part, the exercise movement may include squats, lunges, lateral leg lifts, and the like. The exercise movement is not limited to the above description, and there are no limitations as long as the exercise movement corresponds to an exercise movement for any body part.

2.2.2.3 Video Provision Method

The video provision unit 160 may provide the guide video to the client device 1. When the video provision unit 160 provides the guide video to the client device 1, a user exercise movement video acquired based on the guide video may be acquired at the same time or a different time. After the video provision unit 160 provides the guide video to the client device 1, the video provision unit 160 may acquire the user exercise movement video acquired based on the guide video.

When the user exercise movement video is acquired at the same time as the video provision unit 160 provides the guide video through the client device 1, the client device 1 may provide the guide video and the user exercise movement video in an overlapping manner. When the client device 1 provides the guide video and the user exercise movement video in an overlapping manner, the guide video may be provided with transparency adjusted with respect to that of the user exercise movement video. Also, when the client device 1 provides the guide video and the user exercise movement video in an overlapping manner, the guide video may be provided as a separate guideline which overlaps the user exercise movement and which is added to the user exercise movement in the form of a shape, a line, or the like. As an example, the guide video may be provided as an augmented reality (AR) video.

The video provision unit 160 may normalize the guide video to fit the user's height or body part and then may provide the normalized guide video. As an example, when the height or body part of a trainer who performs the exercise movement included in the guide video differs from the user's height or body part by a predetermined ratio, the video provision unit 160 may normalize the guide video to fit the user's height or body part and then may provide the normalized guide video.

The video provision unit 160 may provide the guide video after adjusting the existence of playback, the degree, the duration, and the like of the guide video through a preset operation. For example, the video provision unit 160 may allow the guide video to be played back through the user standing with open arms or may allow the playback of the guide video to be stopped when the user stands with open arms again. Alternatively, the video provision unit 160 may allow the guide video to be played back through the user standing with open arms and may allow the playback of the guide video to be stopped and allow a guide video including another exercise movement to be provided when the user stands with crossed arms.

Also, the video provision unit 160 may adjust the playback speed of the guide video on the basis of the speed of the user's exercise movement. For example, the video provision unit 160 may adjust the playback speed of the guide video on the basis of the speed of the user's exercise movement. Also, the video provision unit 160 may analyze the speed of the user's exercise movement to adjust the playback speed of the guide video.

The video provision method is not limited to the above description, and at least some of the above description may be modified, deleted, or replaced.

2.3 Exercise Assistance Server 2.3.1 Configuration

Figure 3:
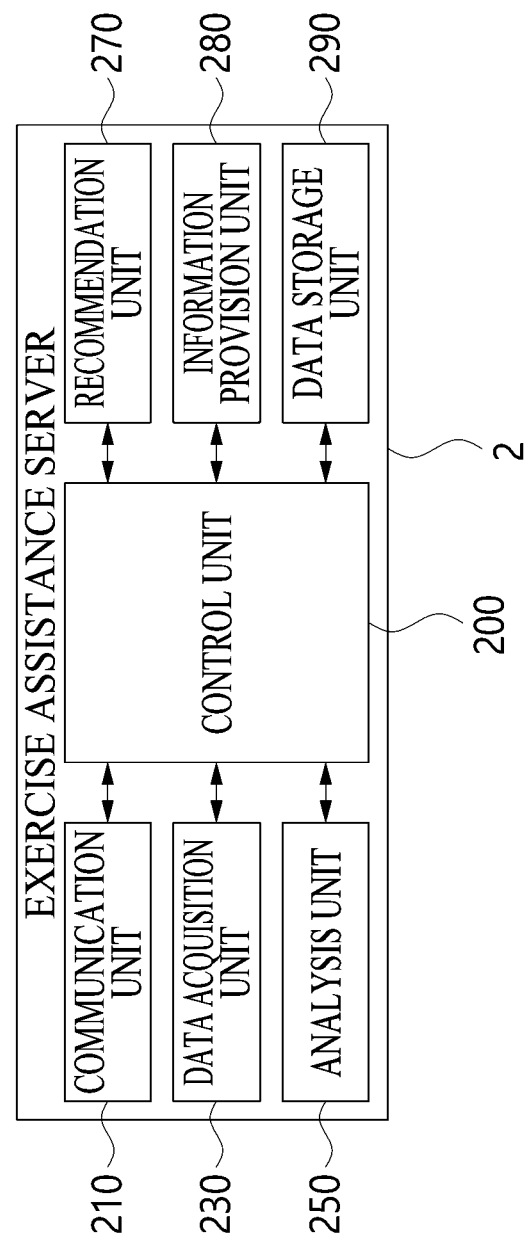
FIG. 3 is a diagram showing a configuration of an exercise assistance server according to an embodiment.

FIG. 3 is a diagram showing a configuration of the exercise assistance server 2 according to an embodiment. The exercise assistance server 2 may include at least one of a control unit 200, a communication unit 210, a data acquisition unit 230, an analysis unit 250, a recommendation unit 270, an information provision unit 280, and a data storage unit 290. However, the configuration of the exercise assistance server 2 is not limited to the above configuration, and some elements may be added or substituted as necessary.

2.3.2 Control Unit

The control unit 200 may control the operation of the exercise assistance server 2. The control unit 200 may control the operation of at least one of the communication unit 210, the data acquisition unit 230, the analysis unit 250, the recommendation unit 270, the information provision unit 280, and the data storage unit 290.

The control unit 200 may include one or more of a CPU, a RAM, a GPU, one or more microprocessors, and other electronic components capable of processing input data according to a predetermined logic. As an example, the control unit 200 may deploy classification or recommendation process data or the like for exercise assistance between the exercise assistance server 2 and the client device 1, which will be described later, on the RAM and may perform various processes according to a deployed program.

2.3.3 Communication Unit

The communication unit 210 may perform a function of enabling the exercise assistance server 2 to receive data input to the client device 1. Also, the communication unit 210 may perform a function of transmitting information provided by the exercise assistance server 2 to the client device 1. Also, the communication unit 210 may perform a function of transmitting analysis and/or recommendation information for data input to the exercise assistance server 2 to the client device 1. The description of the communication unit 210 may be the same as or similar to the description of the client device in Section 2.2 but is not limited to the description of the client device in Section 2.2.

2.3.4 Data Acquisition Unit

The data acquisition unit 230 may acquire data requested for analysis and/or recommendation from the client device 1. The data acquisition unit 230 may acquire video data including the user's exercise movement from the client device 1. The data acquisition unit 230 may acquire data including user information from the client device 1. The data provided from the client device 1 may include information regarding the user's gender, age, health status, BMI information, exercise cycle, exercise amount, exercise intensity, and the like.

The data acquisition unit 230 may process and acquire the data requested for analysis and/or recommendation from the client device 1. The data acquisition unit 230 may selectively acquire only some data suitable for the analysis and/or recommendation from the client device 1 among the data requested for analysis and/or recommendation. The data acquisition unit 230 may separately acquire the data requested for analysis and/or recommendation from the client device 1 on a frame basis and may selectively acquire only at least some of a plurality of frames constituting the data. As an example, the data acquisition unit 230 may acquire some data obtained by editing a part of the video data acquired from the client device 1 in which the user performs an exercise movement.

Also, the data acquisition unit 230 may acquire video data including only a portion of the user's body for which the user performs an exercise movement among the video data acquired from the client device 1. Also, even if the video data acquired from the client device 1 is video data including only a portion of the user's body, the data acquisition unit 230 may acquire the video data as analysis data when the video data is suitable for analyzing the user's exercise movement.

However, the data acquired by the data acquisition unit 230 is not limited to the above description, and there are no limitations as long as the data acquired by the data acquisition unit 230 is suitable for the exercise assistance server 2 to provide analysis and/or recommendation information.

2.3.5 Analysis Unit 2.3.5.1 Overview

Figure 4:
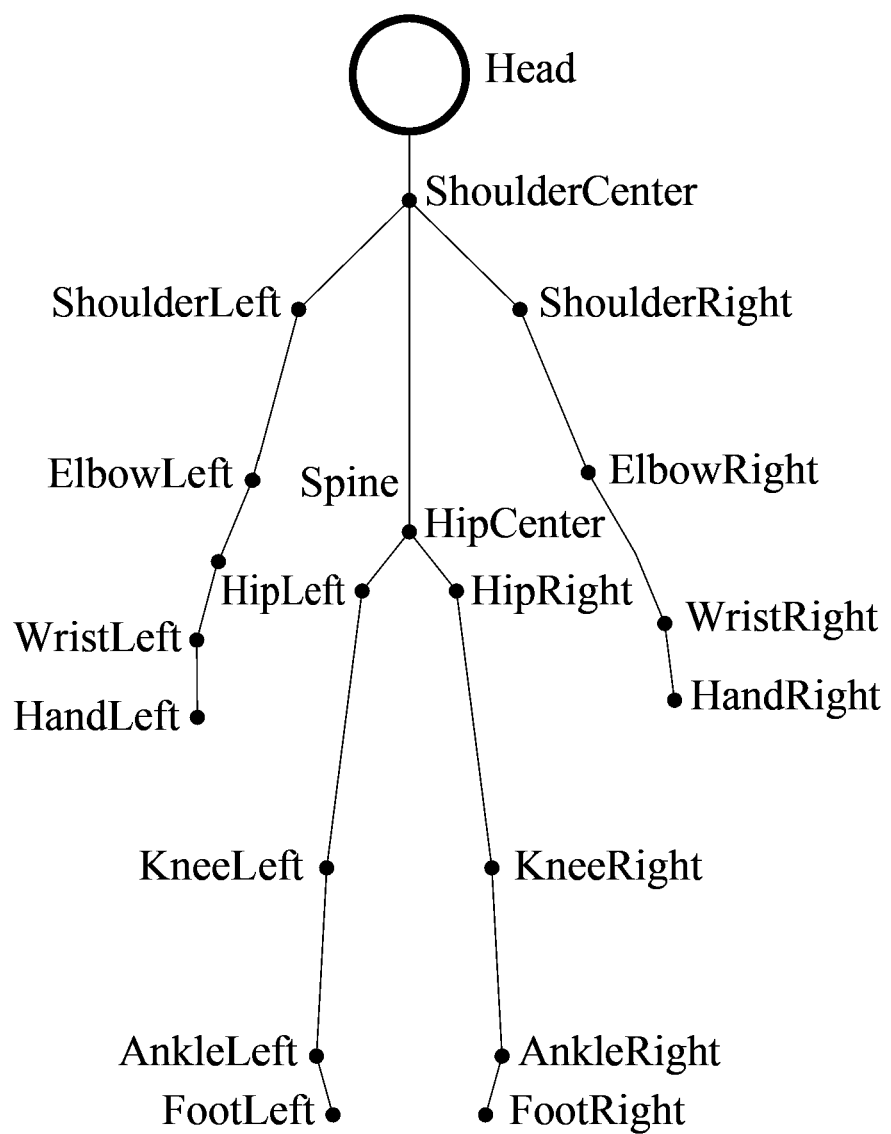
FIG. 4 is a diagram showing skeleton information included in body data according to an embodiment.

FIG. 4 is a diagram showing skeleton information included in body data according to an embodiment. The skeleton information may include information regarding a plurality of joint parts included in a body. As shown in FIG. 4, the skeleton information may include information regarding at least one of a head, a shoulder center, a left shoulder, a right shoulder, a left elbow, a right elbow, a left wrist, a right wrist, a hip center, a left hip, a right hip, a left knee, a right knee, a left ankle, a right ankle, a left foot, a right foot, and the like.

The analysis unit 250 may analyze the movement of the body through the position and/or arrangement of a plurality of joint parts included in the body based on the skeleton information. Thus, the exercise assistance server 2 may easily analyze the user's exercise movement by quickly extracting the user's exercise movement on the basis of the skeleton information.

The analysis unit 250 may perform an analysis by using a predetermined algorithm. The analysis unit 250 may perform an analysis by using a predetermined computer program. The analysis unit 250 may perform an analysis by using artificial intelligence (AI). The analysis unit 250 may perform an analysis by using AI that is trained with a plurality of pieces of data. Also, the analysis unit 250 may use Scale Invariant Feature Transform (SIFT), Histogram of Oriented Gradient (HOG), Haar feature, Ferns, Local Binary Pattern (LBP), Modified Census Transform (MCT), Neural Network (NN), Deep Neural Network (DNN), Convolutional Neural Network (CNN), etc.

2.3.5.2 Video Analysis Method

The analysis unit 250 may analyze data acquired by the data acquisition unit 230 on the basis of the skeleton information. The analysis unit 250 may extract a plurality of joint parts on the basis of the skeleton information and analyze the data acquired by the data acquisition unit 230. Also, the analysis unit 250 may determine whether the user's exercise movement is similar to the guide video through data analysis based on the skeleton information. Also, the analysis unit 250 may perform an evaluation on the user's exercise movement through the determination of similarity of the user's exercise movement included in data to be analyzed.

Figure 5:
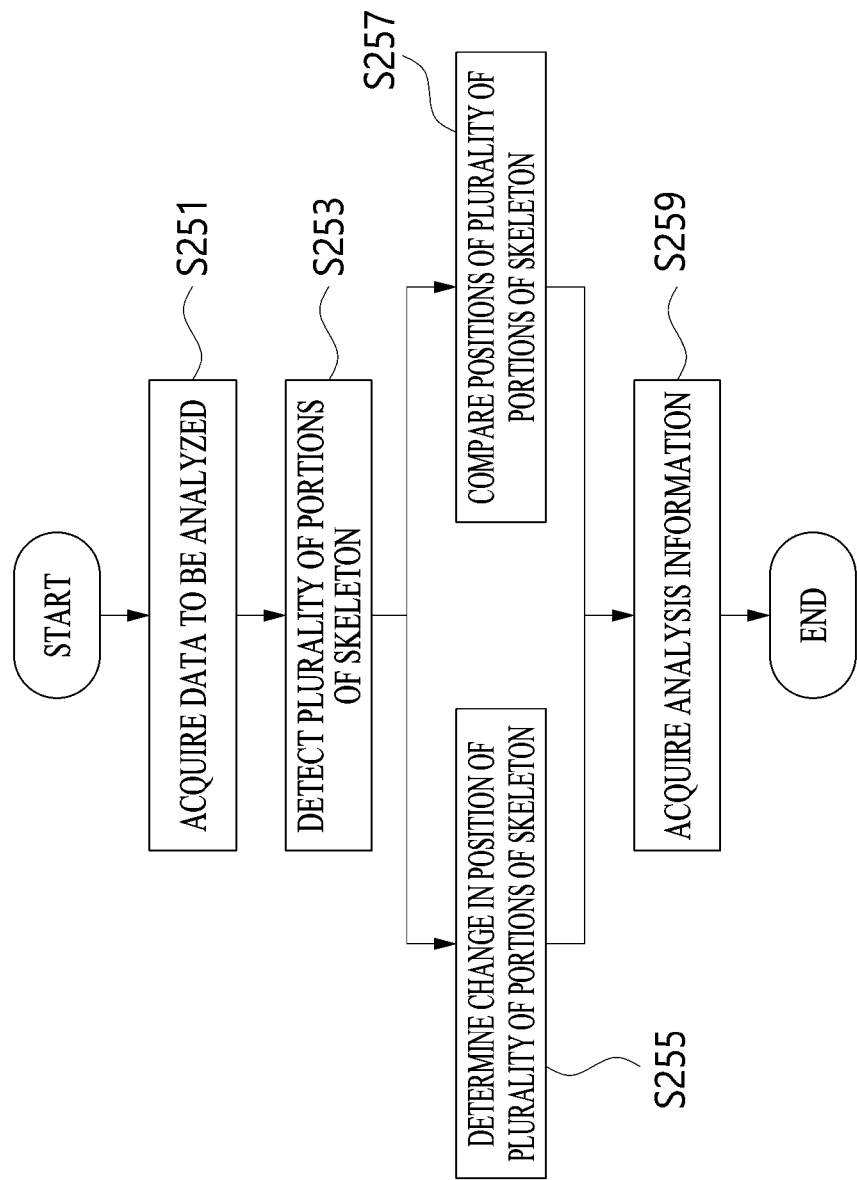
FIG. 5 is a diagram showing an analysis method of an exercise assistance device according to an embodiment.

FIG. 5 is a diagram showing an analysis method of an exercise assistance device according to an embodiment. The video analysis method may include at least one of the acquisition of data to be analyzed (S251), the detection of a plurality of portions of a skeleton (S253), the determination of a change in position of the plurality of portions of the skeleton (S255), the comparison of positions of the plurality of portions of the skeleton (S257), and the acquisition of analysis information (S259). The video analysis method is not limited to the above operations, and some of the operations may be changed or excluded or some operations may be added as necessary.

The acquisition of the data to be analyzed (S251) may be an operation of acquiring data requested for analysis among data acquired by the data acquisition unit 230. The data acquired through the acquisition of data to be analyzed (S251) is the data requested for analysis among the data acquired by the data acquisition unit 230. And the acquisition of data to be analyzed (S251) may include operation of acquiring partially processed data The detection of the plurality of portions of the skeleton (S253) may be an operation of detecting (extracting) the plurality of portions of the skeleton from the user's body included in the data acquired through the acquisition of the data to be analyzed (S251). The detection of the plurality of portions of the skeleton (S253) may include extracting two-dimensional (2D) joint information by detecting (extracting) the plurality of portions of the skeleton included in the data acquired through the acquisition of data to be analyzed (S251). The detection of the plurality of portions of the skeleton (S253) may include extracting information regarding a plurality of joints, to each of which adjacent portions of the skeleton are connected, from the 2D joint information. As an example, referring to FIGS. 4 and 5, the detection of the plurality of portions of the skeleton (S253) may include extracting joint information such as a first joint to which the head and the should center are connected, a second joint to which the shoulder center and the right shoulder are connected, a third joint to which the shoulder center and the left shoulder are connected, and the like. Also, the detection of the plurality of portions of the skeleton (S253) may include converting the 2D joint information into three-dimensional (3D) joint information to extract the above-described joint information.

Also, when the data acquired through the acquisition of the data to be analyzed (S251) is video data including only a portion of the user's body among the video data acquired from the client device 1, the detection of the plurality of portions of the skeleton (S253) may include detecting portions of the skeleton in a portion of the user's body included in the video data and matching a plurality of virtually detected portions of the skeleton to the other portion of the user's body. Also, in this case, the detection of the plurality of portions of the skeleton (S253) may include detecting portions of the skeleton in only a portion of the user's body included in the video data, detecting only corresponding portions of the skeleton in the guide video, and performing a comparison therebetween.

The determination of the change in position of the plurality of portions of the skeleton (S255) may be an operation of determining a change in position of the portions of the skeleton on the basis of the information regarding the plurality of portions of the skeleton detected through the detection of the plurality of portions of the skeleton (S253). The determination of the change in position of the plurality of portions of the skeleton (S255) may be an operation of analyzing a change in position of each portion of the skeleton on the basis of the information regarding the plurality of portions of the skeleton acquired for each frame of the data acquired through the acquisition of the data to be analyzed (S251) and thus determining the user's movement through portions of the skeleton which have changed in position. Since the determination of the change in position of the plurality of portions of the skeleton (S255) may include determining the user's movements through the portions of the skeleton which have changed in position as described above, it is possible to automatically extract the number of the user's exercise movements, and thus the user may not perform a separate operation of inputting the number of movements.

The comparison of the positions of the plurality of portions of the skeleton (S257) may be an operation of comparing the positions of the portions of the skeleton on the basis of the information regarding the plurality of portions of the skeleton detected through the detection of the plurality of portions of the skeleton (S253). The comparison of the positions of the plurality of portions of the skeleton (S257) may be an operation of performing a position comparison between the data acquired through the acquisition of the data to be analyzed (S251) and the guide video described in Section 2.2.2.2 Guide Video on a frame basis. Frame-based skeleton position data included in the guide video may be stored in the data storage unit 290. When the comparison of the positions of the plurality of portions of the skeleton (S257) includes performing a position comparison between the data acquired through the acquisition of the data to be analyzed (S251) and the guide video on a frame basis, the comparison may be performed after operating times included in the video and data are normalized.

Also, the comparison of the positions of the plurality of portions of the skeleton (S257) may include comparing values obtained by extracting joint vector values from the guide video and the data acquired through the acquisition of the data to be analyzed (S251) and then by normalizing the extracted joint vector values. Also, the comparison of the positions of the plurality of portions of the skeleton (S257)

may include normalizing the guide video and the data acquired through the acquisition of the data to be analyzed (S251) through the Dynamic Time Warping (DTW) algorithm to perform the comparison. Also, the comparison of the positions of the plurality of portions of the skeleton (S257) may perform similarity determination on the basis of the average similarity of the plurality of joint vectors by using the following equation:

$$\theta = \cos^{-1}\left(\frac{A \cdot B}{|A||B|}\right)$$

$$\text{Similarity} = \left(100 - \frac{|\theta - \theta'|}{|\theta'|} * 100\right)(\%)$$

where θ is an angle between a joint vector of the data to be analyzed and a joint vector of the guide video, and θ' is a predetermined threshold value.

The acquisition of the analysis information (S259) may be an operation of acquiring analysis information obtained through the detection of the plurality of portions of the skeleton (S253). The acquisition of the analysis information (S259) may be an operation of acquiring analysis information obtained through at least one of the determination of the change in position of the plurality of portions of the skeleton (S255) and the comparison of positions of the plurality of portions of the skeleton (S257).

2.3.5.3 Analysis Information

The analysis unit 250 may acquire the analysis information through the above-described video analysis method. The analysis information may be analysis information regarding a user exercise video included in the data acquired by the data acquisition unit 230. The analysis information may include the accuracy, number of repetitions, movement duration, movement performance speed, performance capability for each body part, and the like of the user's exercise movement. The analysis information may include information obtained by analyzing the accuracy, number of repetitions, movement duration, movement performance speed, performance capability for each body part, and the like of the user's exercise movement through a comparison to the guide video. The analysis information may include evaluation information for the user's exercise movement, and the evaluation information may be provided to the user in various forms.

The analysis unit 250 may perform a comparison to the guide video through the video data including the user's exercise movement, and thus it is possible to improve the accuracy of the evaluation on the user's exercise movement. Also, the analysis unit 250 may perform a comparison to the guide video through an analysis method for detecting portions of the skeleton for the user's exercise movement, and thus it is possible to more easily and quickly perform an evaluation on the user's exercise movement.

2.3.6 Recommendation Unit 2.3.6.1 Overview

The recommendation unit 270 may perform a function of recommending an exercise movement suitable for a user. The recommendation unit 270 may perform a function of recommending an exercise movement suitable for a user on the basis of the data acquired by the data acquisition unit 230. The recommendation unit 270 may perform a function of recommending the exercise movement suitable for the user on the basis of at least one of the data acquired by the data acquisition unit 230 and the analysis information acquired by the analysis unit 250.

The exercise assistance device may provide convenience when the user performs an exercise movement as the recommendation unit 270 recommends an exercise movement suitable for the user. Also, the recommendation unit 270 may provide a personalized exercise set by recommending exercise movements required for each user on the basis of the analysis information regarding the user's exercise movement. Thus, the user can be provided with a personal training service at a lower price.

The recommendation unit 270 may perform a recommendation through a predetermined algorithm. Also, the recommendation unit 270 may perform a recommendation by using a predetermined computer program. The recommendation unit 270 may perform a recommendation by using AI. Also, the recommendation unit 270 may perform a recommendation by using AI that is trained with a plurality of pieces of data. Also, the recommendation unit 270 may perform a recommendation by using a Neural Network (NN), Deep Neural Network (DNN), Convolutional Neural Network (CNN), and the like. Also, the recommendation unit 270 may perform a recommendation by using an artificial neural network that recognizes patterns of time-series data, such as Recurrent Neural Networks (RNN) and Long Short-Term Memory (LSTM).

In particular, when the recommendation unit 270 performs a recommendation by using an artificial neural network such as RNN or LSTM, the recommendation unit 270 may perform a function of recommending an exercise movement suitable for the user in consideration of previously input user exercise videos in addition to the input user exercise video.

2.3.6.2 Recommendation Method

Figure 6:
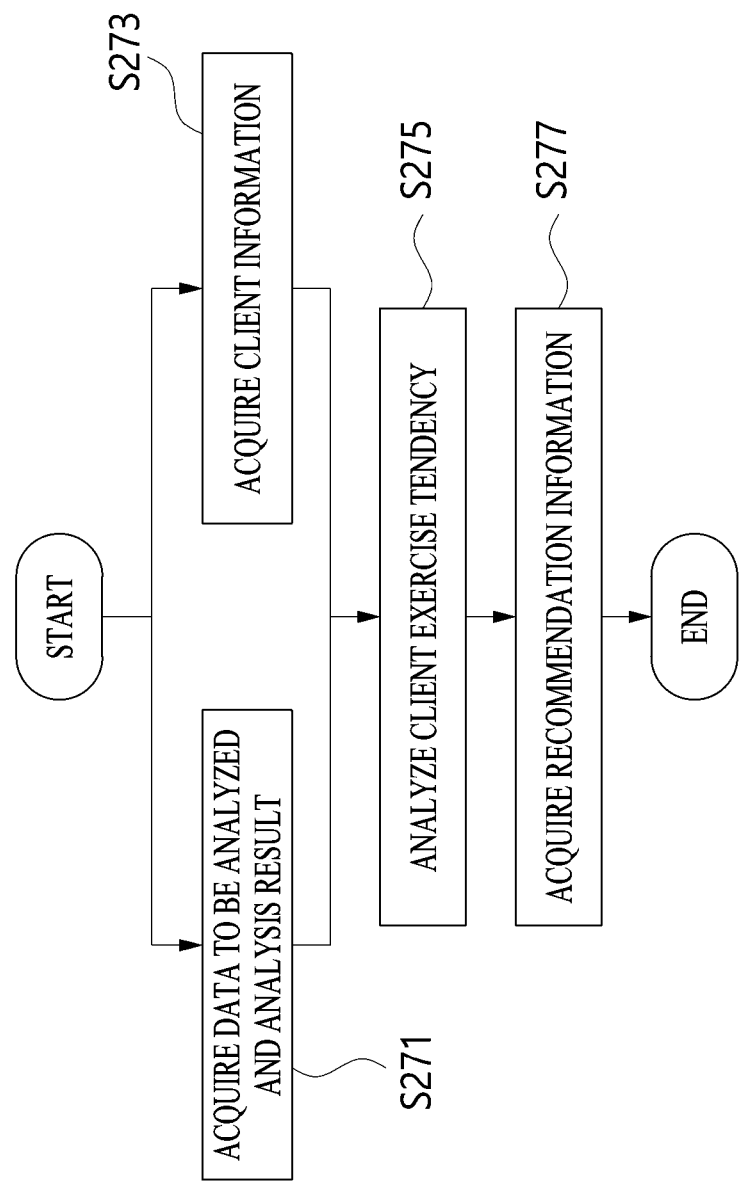
FIG. 6 is a diagram showing a recommendation method of an exercise assistance device according to an embodiment.

FIG. 6 is a diagram showing a recommendation method of an exercise assistance device according to an embodiment. The recommendation method may include the acquisition of data to be analyzed and an analysis result (S271), the acquisition of client information (S273), the analysis of a client exercise tendency (S275), and the acquisition of recommendation information (S277). The recommendation method is not limited to the above operations, and some of the operations may be changed or excluded or some operations may be added as necessary.

The acquisition of the data to be analyzed and the analysis result (S271) may be an operation of acquiring information obtained through an analysis in the analysis unit 250 or acquiring analysis information prestored in the exercise assistance server 2. The acquisition of the data to be analyzed and the analysis result (S271) may be an operation of acquiring the data to be analyzed and the analysis result from the analysis unit 250. The acquisition of the data to be analyzed and the analysis result (S271) may be an operation of acquiring the data to be analyzed and the analysis result from the analysis unit 250 as analysis information. The acquisition of the data to be analyzed and the analysis result (S271) may be an operation of performing an acquisition for each exercise movement or for each predetermined exercise item.

The acquisition of the client information (S273) may be an operation of acquiring information input from the client device 1 or acquiring information prestored in the client device 1. The acquisition of the client information (S273) may be an operation of acquiring information regarding a user who uses the exercise assistance device. The acquisition of the client information (S273) may include acquiring, as the information of the user, information regarding the user's gender, age, health status, BMI information, exercise cycle, exercise amount, exercise intensity, and the like. Also, the acquisition of the client information (S273) may include acquiring the user's analysis and/or recommendation information prestored in the exercise assistance server 2.

The analysis of the client exercise tendency (S275) may include analyzing the user's exercise tendency on the basis of information acquired from at least one of the acquisition of the data to be analyzed and the analysis result (S271) and the acquisition of the client information (S273). The analysis of the client exercise tendency (S275) may include analyzing the user's exercise tendency such as exercise habits, flexibility, balance, performance capability, and the like on the basis of information acquired from at least one of the acquisition of the data to be analyzed and the analysis result (S271) and the acquisition of the client information (S273).

The acquisition of the recommendation information (S277) may perform a function of acquiring recommendation information suitable for the user on the basis of the information performed through the analysis of the client exercise tendency (S275). The acquisition of the recommendation information (S277) may perform a function of acquiring recommendation information for exercise movements suitable for the user's exercise habits, flexibility, balance, performance capability, and the like on the basis of the information performed through the analysis of the client exercise tendency (S275).

2.3.6.3 Recommendation Information

The recommendation unit 270 may provide recommendation information to a user, and the user may perform a suitable exercise movement on the basis of the recommendation information. In this regard, it is possible to improve the user's exercise efficiency.

The recommendation information may be an exercise set consisting of exercise movements suitable for the user among a plurality of exercise movements. Also, when the recommendation information is an exercise set consisting of exercise movements suitable for the user among a plurality of exercise movements, the exercise set may be provided in a sequence suitable for the user. Also, the recommendation information may be provided in consideration of an exercise cycle, exercise amount, exercise duration, and the like suitable for the user. Also, the recommendation information includes a plurality of set candidates, each of which consists of exercise movements suitable for the user among the plurality of exercise movements, and the plurality of set candidates may be sequentially provided according to the level of recommendation of the recommendation unit 270 or according to the user's selection.

Also, the recommendation information may be movement recommendation information for guiding instructions or corrections on the basis of the degree of similarity of the user's exercise movement which is determined from the analysis information. The movement recommendation information may be information for partially guiding instructions or corrections for an exercise movement with low accuracy among performed exercise movements. Alternatively, the movement recommendation information may be information for repeatedly performing an exercise movement with low accuracy among performed exercise movements.

Also, the recommendation information may be information for modifying and proposing the intensity and/or number of exercise movements on the basis of the performance capability of the user's exercise movement determined from the analysis information. When the performance capability of the user's exercise movement determined from the analysis information is similar to that of the guide video above a predetermined reference, the recommendation information may be information for increasing the intensity and/or number of exercise movements or recommending other exercise movements. On the other hand, when the performance capability is similar to that of the guide video below a predetermined reference, the recommendation information may be information for decreasing the intensity and/or numbers of exercise movements or recommending partial exercise movements to perform only the most dissimilar movements.

The details of the recommendation information provided to the client device 1 will be described in detail in Section 4 User Interface.

2.3.7 Information Provision Unit

The information provision unit 280 may provide information acquired from at least one of the data acquisition unit 230, the analysis unit 250, and the recommendation unit 270 to the client device 1. The information provision unit 280 may provide, to the client device 1, information acquired from at least one of the data to be analyzed which is acquired by the data acquisition unit 230, the analysis information which is acquired by the analysis unit 250, and the recommendation information which is acquired by the recommendation unit 270. The information provision unit 280 may collect information determined as being suitable for the user among the information acquired from at least one of the data to be analyzed which is acquired by the data acquisition unit 230, the analysis information which is acquired by the analysis unit 250, and the recommendation information which is acquired by the recommendation unit 270 and may provide the collected information to the client device 1.

Also, the information provision unit 280 may regularly provide the analysis information acquired by the analysis unit 250 and/or the recommendation information acquired by the recommendation unit 270 to the user in the form of a report. Also, the information provision unit 280 may regularly provide the analysis information and/or the recommendation information to the user in the form of a daily report or a monthly report. Also, the information provision unit 280 may provide a personalized fitness service using accumulated data regarding the analysis information and/or recommendation information, thereby providing a user motivation and record management service.

2.3.8 Data Storage Unit

The data storage unit 290 may store information acquired from at least one of the data acquisition unit 230, the analysis unit 250, and the recommendation unit 270. The data storage unit 290 may store information acquired from at least one of the data to be analyzed which is acquired by the data acquisition unit 230, the analysis information which is acquired by the analysis unit 250, and the recommendation information which is acquired by the recommendation unit 270. The data storage unit 290 may collect information determined as being suitable for the user among the information acquired from at least one of the data to be analyzed which is acquired by the data acquisition unit 230, the analysis information which is acquired by the analysis unit 250, and the recommendation information which is acquired by the recommendation unit 270 and may store the collected information in the client device 1.

Figure 7:
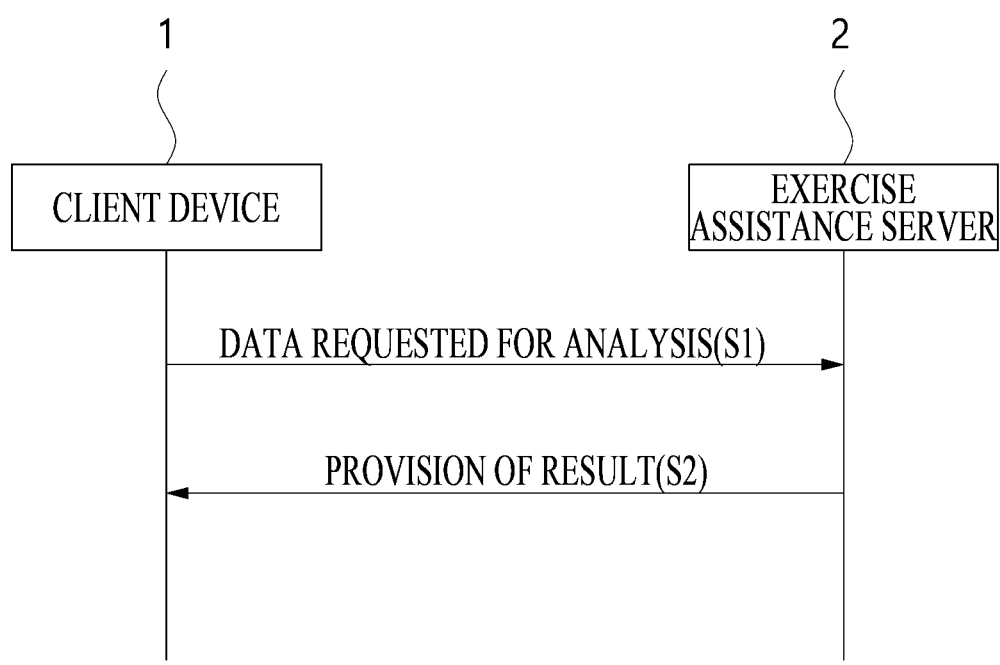
FIG. 7 is a diagram showing an exercise assistance process according to an embodiment.

3. Exercise Assistance Process Based on Exercise Assistance Server 3.1 Overall Process FIG. 7 is a diagram showing an exercise assistance process according to an embodiment. The exercise assistance process is performed by the client device 1 and the exercise assistance server 2 and may include at least one of a data-requested-for-diagnosis operation (S1) and a data provision operation (S2).

In the data-requested-for-diagnosis operation (S1), data requested for diagnosis may be received from the client device 1 or may be delivered or transmitted to the exercise assistance server 2. Also, the data requested for diagnosis may be analyzed and/or recommended by the exercise assistance server 2 in the data-requested-for-diagnosis operation (S1), and the data provision operation (S2) may be performed for the client device 1 by the exercise assistance server 2.

3.2 Analysis Process

Figure 8:
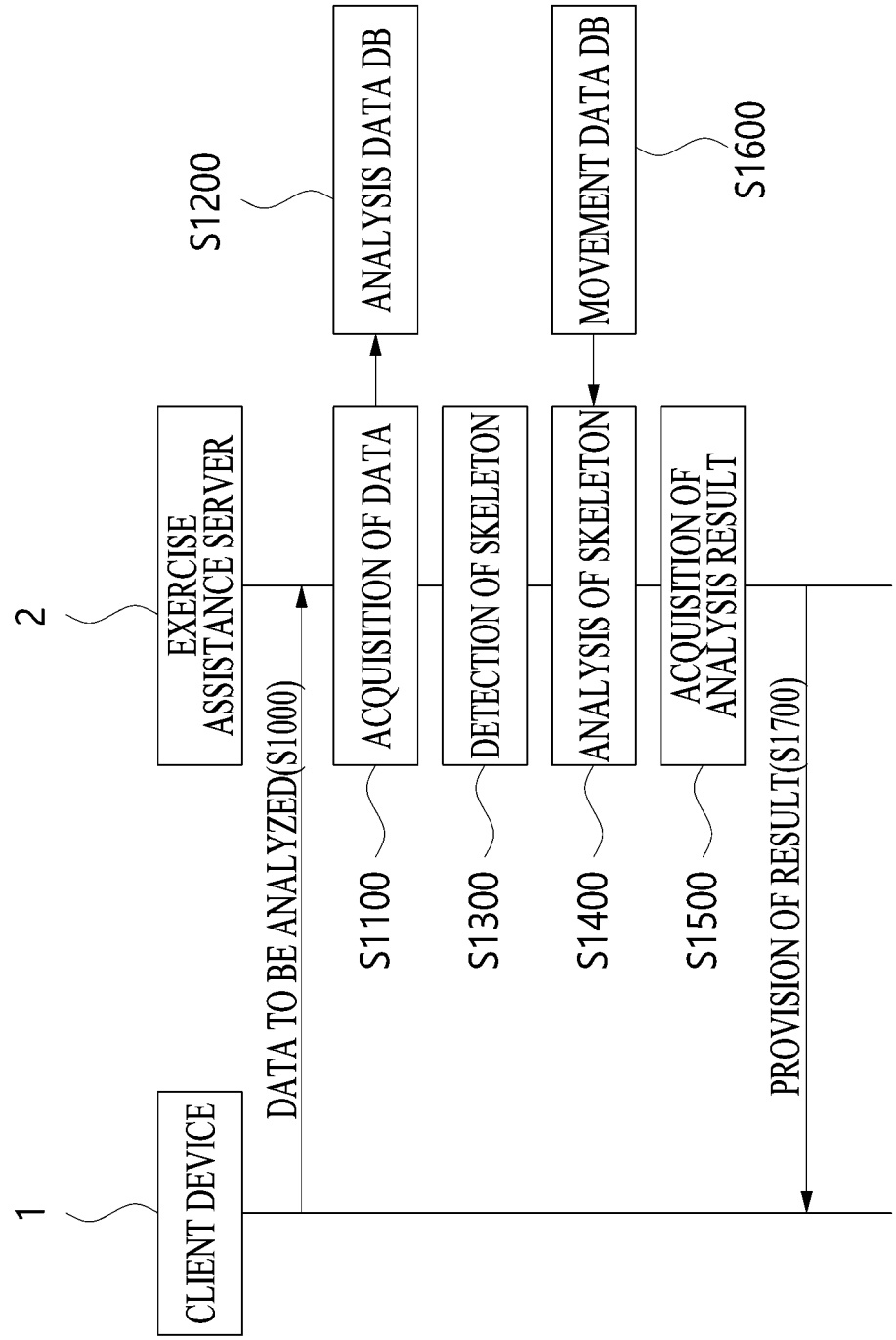
FIG. 8 is a diagram showing an analysis process according to an embodiment.

FIG. 8 is a diagram showing an analysis process according to an embodiment. The analysis process is performed by the client device 1 and the exercise assistance server 2 and may include at least one of a data-to-be-analyzed operation (S1000), a data acquisition operation (S1100), an analysis data database (DB) operation (S1200), a skeleton detection operation (S1300), a skeleton analysis operation (S1400), an analysis result acquisition operation (S1500), a movement data DB operation (S1600), and a result provision operation (S1700).

In the data-to-be-analyzed operation (S1000), data to be analyzed may be received from the client device 1 or may be delivered or transmitted to the exercise assistance server 2. Also, in the data acquisition operation (S1100), the exercise assistance server may acquire at least a portion of the data to be analyzed, and the data acquired through the data acquisition operation (S1100) may be stored in an analysis data DB (S1200). Also, in the skeleton detection operation (S1300), skeleton detection may be performed on the data acquired through the data acquisition operation (S1100). Also, the skeleton analysis operation (S1400) may be performed on the basis of a plurality of portions of a skeleton detected through the skeleton detection operation (S1300). Also, the skeleton analysis operation (S1400) may be performed on the basis of a comparison between a plurality of exercise movements provided by the movement data DB (S1600). The analysis result acquisition operation (S1500) may include acquiring a result of the analysis performed through the skeleton analysis operation (S1400). A result of the analysis performed through the analysis result acquisition operation (S1500) may be stored in the analysis data DB (S1200) in addition to the data to be analyzed (S1100). In the result provision operation (S1700), the analysis result acquired through the analysis result acquisition operation (S1500) may be provided. In the result provision operation (S1700), a result of an analysis performed on the basis of a comparison to the plurality of exercise movements provided in the movement data DB (S1600) may be provided.

3.3 Recommendation Process

Figure 9:
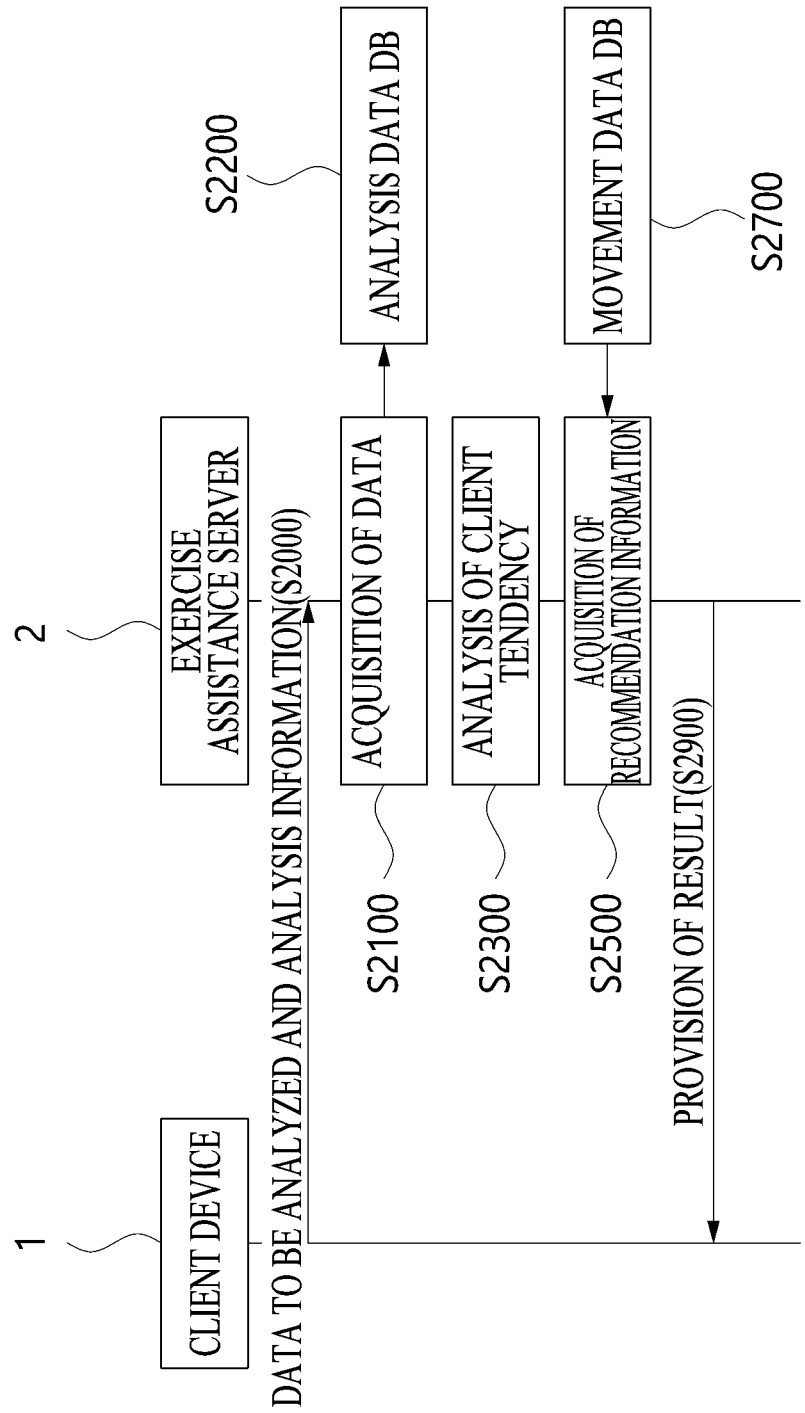
FIG. 9 is a diagram showing a recommendation process according to an embodiment.

FIG. 9 is a diagram showing a recommendation process according to an embodiment. The recommendation process is performed by the client device 1 and the exercise assistance server 2 and may include at least one of a data-to-be-analyzed-and-analysis-information operation (S2000), a data acquisition operation (S2100), an analysis data DB operation (S2200), a client tendency analysis operation (S2300), a recommendation information acquisition operation (S2500), a movement data DB operation (S2700), and a result provision operation (S2900).

In the data-to-be-analyzed-and-analysis-information operation (S2000), data to be analyzed and analysis information may be provided from the client device 1 to the exercise assistance server 2. Also, in the data acquisition operation (S2100), the exercise assistance server 2 may acquire data based on a recommendation process from the analysis data DB (S2200) together with the data to be analyzed and the analysis information (S2000) provided from the client device 1. In the client tendency analysis operation (S2300), the user's exercise tendency may be analyzed on the basis of the data acquired through the data acquisition operation (S2100). Also, in the recommendation information acquisition operation (S2500), recommendation information for recommending exercise movement suitable for the user may be acquired from the movement data DB (S2700) on the basis of the information acquired through the client tendency analysis operation (S2300). In the result provision operation (S2900), the recommendation result acquired through the recommendation information acquisition operation (S2600) may be provided. In the result provision operation (S2900), in particular, an exercise movement suitable for the user in the movement data DB (S2700) may be provided as a recommendation result.

4. User Interface

According to an embodiment, the client device 1 may have a display unit for providing the analysis information and/or recommendation information to the user. In this case, the display unit may be configured to clearly deliver the analysis information and/or recommendation information to the user so that the user can easily use the analysis information and/or recommendation information.

As an example of the display unit, a display for providing visual information to the user may be provided. In this case, a graphic user interface for visually delivering the analysis information and/or the recommendation information to the user may be used.

FIGS. 10 to 15 are diagrams showing a user interface of an exercise assistance device according to an embodiment. Some embodiments of the user interface which can be used in the exercise assistance device will be described with reference to FIGS. 10 to 15.

Figure 10:
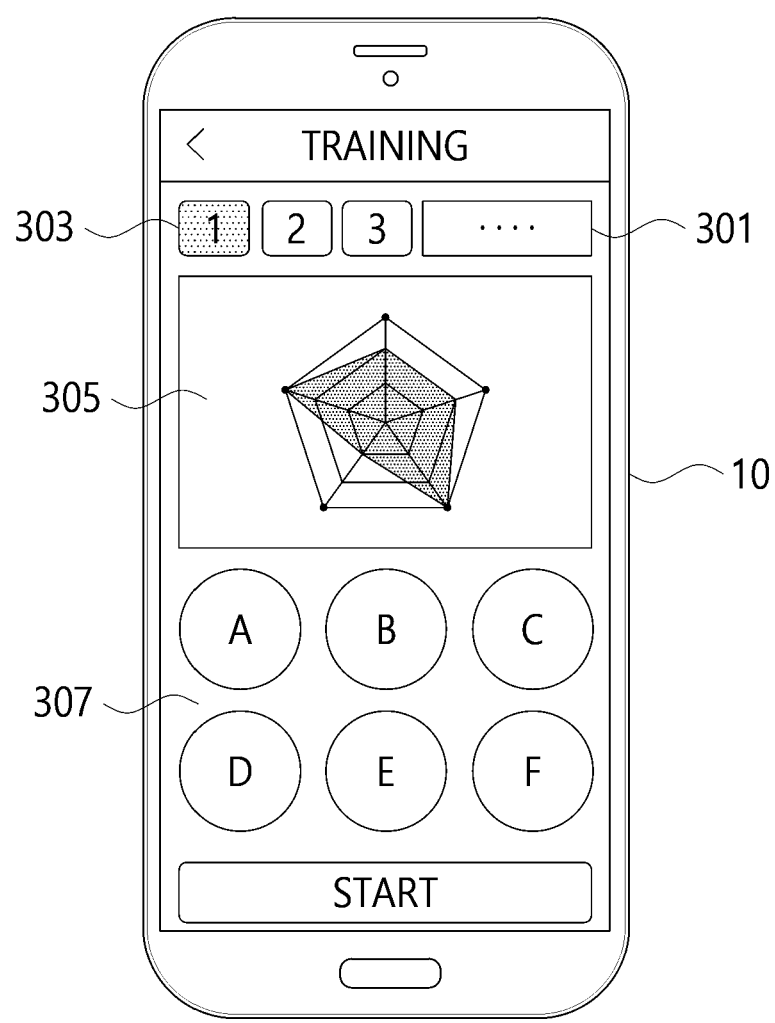
FIGS. 10 to 15 are diagrams showing a user interface of an exercise assistance device according to an embodiment.

FIG. 10 is a diagram showing a user interface of a training recommendation list according to an embodiment. Referring to FIGS. 1 to 10, the client device 1 may display a training recommendation list on a display 10.

The client device 1 may display a plurality of training sets 303 as the training recommendation list on the display 10 so that one of the plurality of training sets 303 can be selected. When none of the plurality of training sets 303 is suitable for a user's preference, a reset button 301 providing other sets may be displayed. Also, when the user selects one of the plurality of training sets 303, the client device 1 may display a diagram 305 that indicates weight (or stimulation level) of exercise for each body part for the selected training set 303. On the diagram 305, the weight(or stimulation level) of exercise for each body part may be marked on the line of the diagram 305, and the higher the weight(or stimulation level) of exercise for each body part is, the higher line the mark of the weight(or stimulation level) may locate in. And the weight (or stimulation level) of exercise for each body part may be expressed in a region based on the mark of the weight (or stimulation level) on the diagram 305. The weight (or stimulation level) may be different according to the kind of exercise, and the area of the region may be different according to the kind of exercise. In addition, the client device 1 may list and display an exercise movement list 307 for the selected training set 303. The exercise movement list 307 may be displayed in the form of an image, text, video, icon, and the like.

Figure 11:
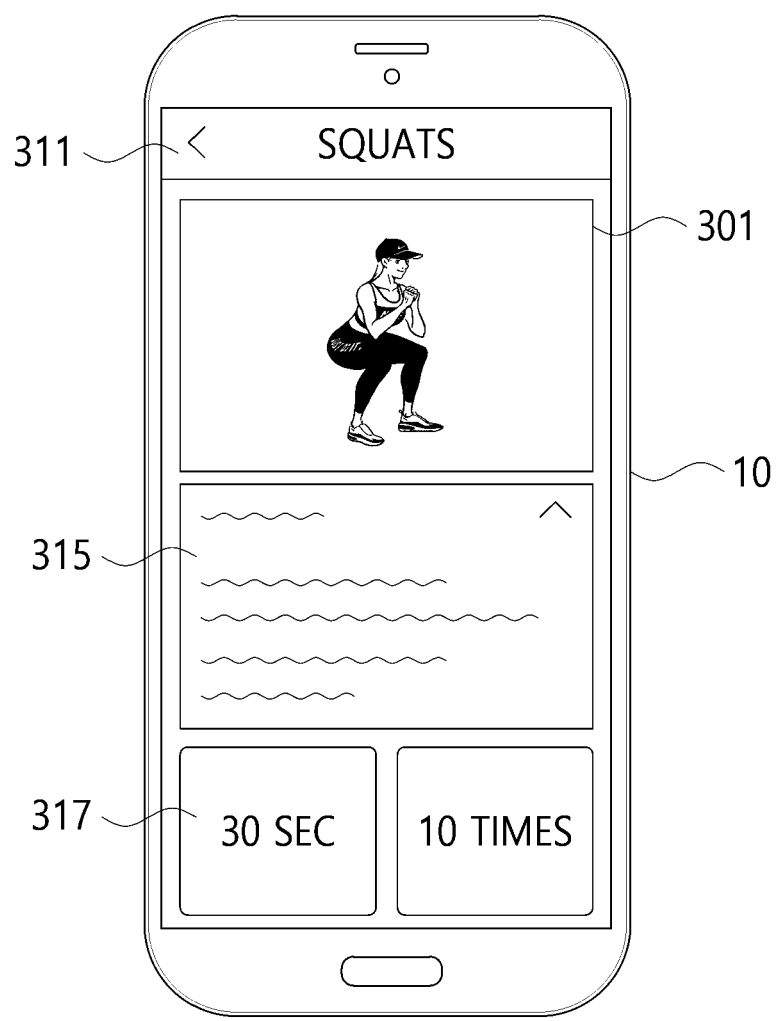
Figure 12:
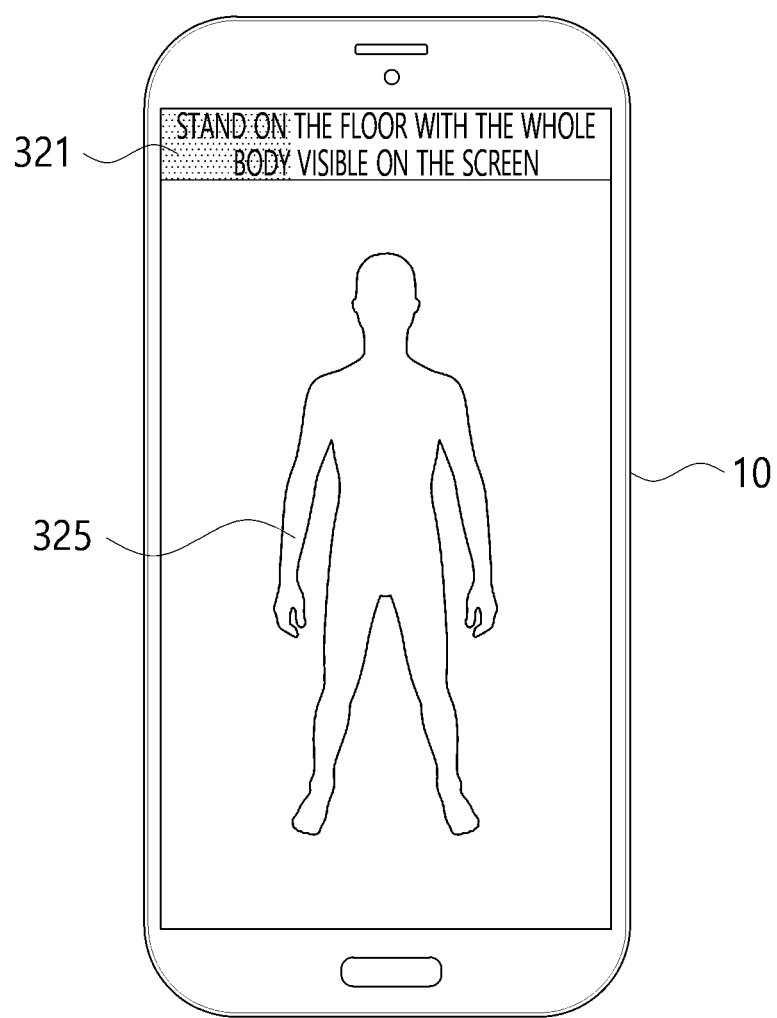
Figure 13:
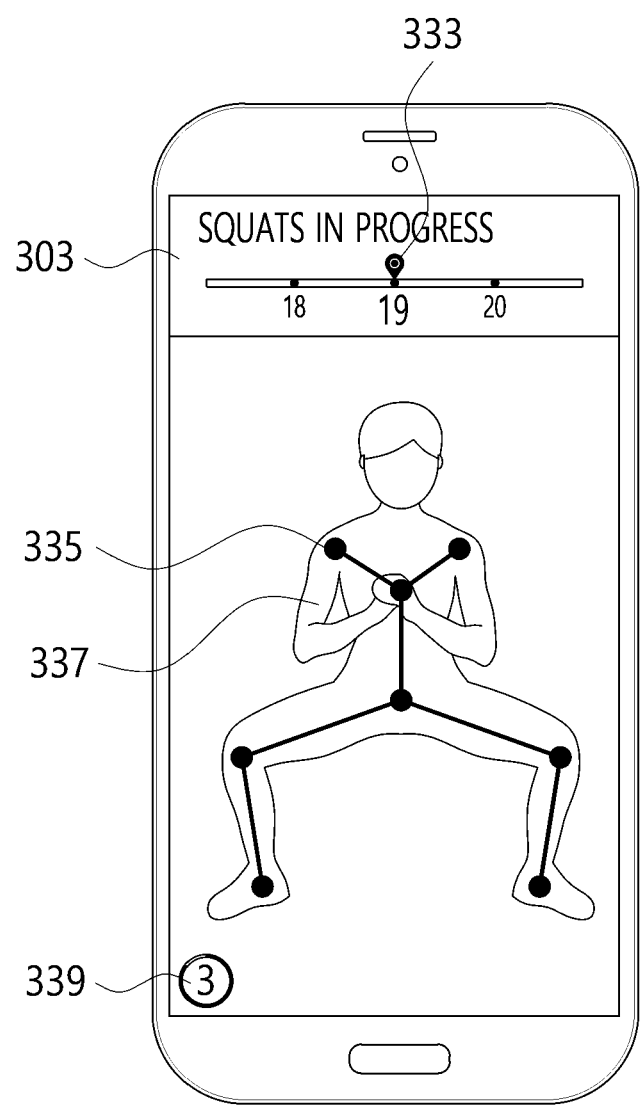

FIGS. 11 to 13 are diagrams showing a user interface for the user's exercise video and the guide video. Referring to FIGS. 1 to 13, the client device 1 may display a guide video of an exercise movement on the display 10.

Referring to FIGS. 1 to 11, when the user makes a selection to perform a specific exercise movement 311, the client device 1 may provide exercise information 315 and exercise amount and exercise duration 317 of the corresponding exercise movement to the display 10. The exercise movement may be displayed in the form of an image, text, video, icon, and the like.

Referring to FIGS. 1 to 12, the client device 1 may display, on the display 10, a guideline for the user to capture a video in which a specific exercise movement is performed on the basis of the guide video. The guideline may be displayed as an instruction 321 in a text form, and where the user should be positioned may be indicated by a shape or line 325.

Also, referring to FIGS. 1 to 13, the guide video may be overlapped with the user's exercise performance video and displayed on the display 10. The progress degree 303 of the guide video may be displayed together with text, and the progress degree 303 of the guide video may be displayed by a number, a timeline, a time bar, or the like. Also, the guide video 335 is overlapped with the user's exercise video 337 and may be displayed in an overlapping manner as a predetermined line, shape, dot, and the like. The guide video 335 may be performed in accordance with the progress degree 303 of the guide video and may guide the user to perform the movement according to the progress speed of the guide video 335. Also, the execution time 339 of the exercise movement in the guide video may be displayed by a number, an icon, or the like.

Figure 14:
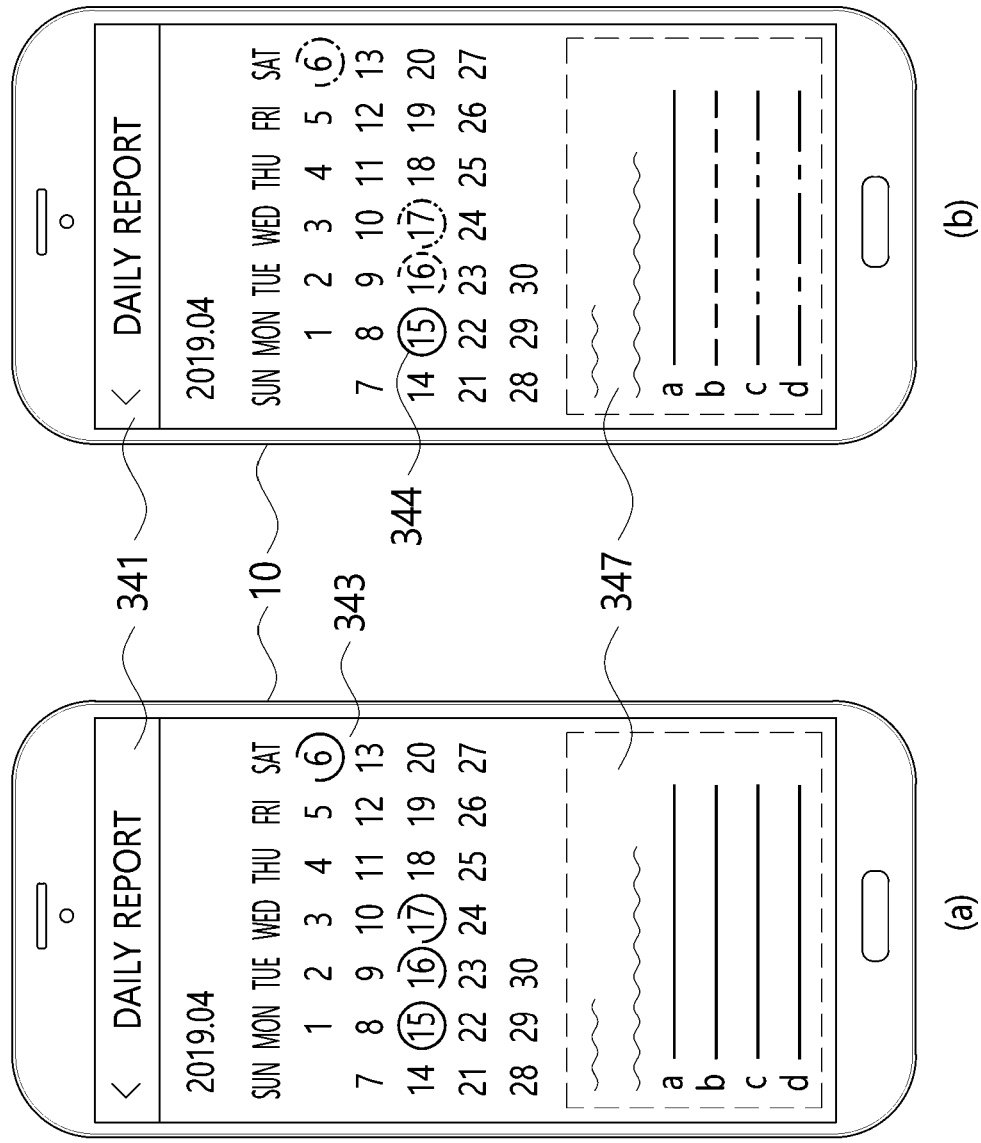
Figure 15:
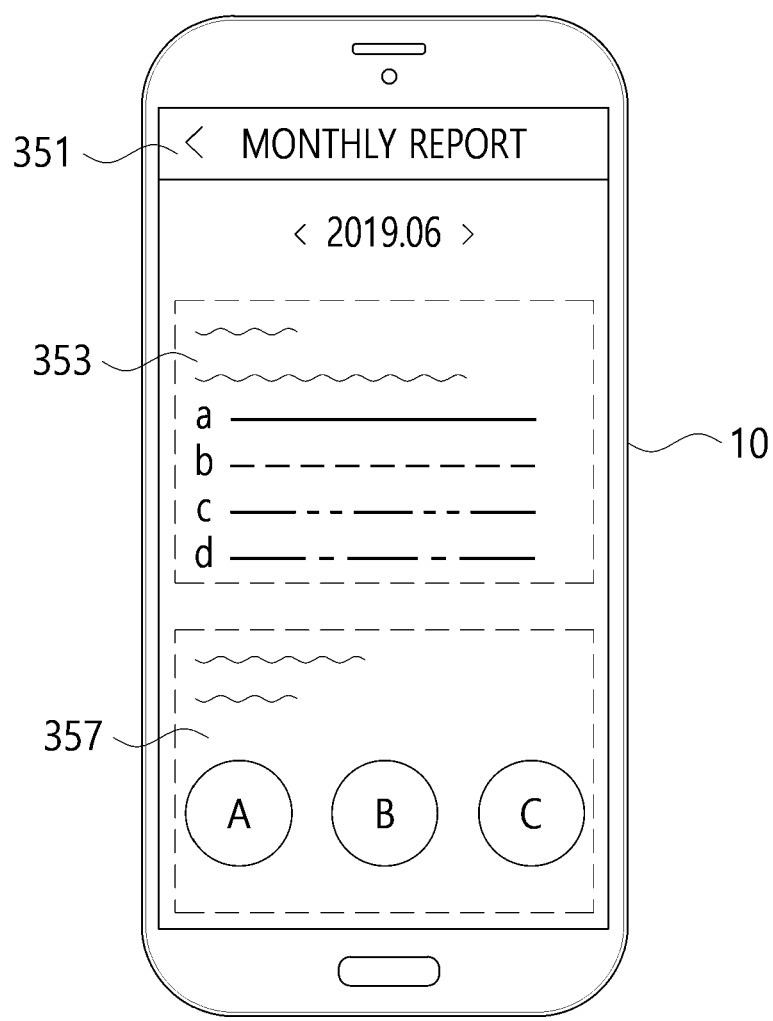

FIGS. 14 and 15 are diagrams showing a user interface of an exercise execution report according to an embodiment. Referring to FIGS. 1 to 15, the client device 1 may display an evaluation report for a user exercise execution video on the display 10.

Referring to FIGS. 1 to 14, the client device 1 may provide a daily report 341 for the user's exercise execution video to the display 10. The client device 1 may display the accuracy 343 of the user's exercise execution video on a calendar or may display a part-specific weight 344 for the user's exercise execution. Also, the client device 1 may display exercise-part-specific evaluations for the user's exercise execution video in the form of text, an icon, an image, etc., and may display a final evaluation obtained by summing the evaluations for the parts.

Referring to FIGS. 1 to 15, the client device 1 may provide a monthly report 351 for the user's exercise execution video to the display 10. The client device 1 may display a total exercise duration, an evaluation for each exercise part, average accuracy, total burned calories, and the like in the form of text, icons, and the like as a total evaluation 353 of the user's exercise video which is analyzed on a monthly basis. Also, the client device 1 may display a monthly total exercise result 357 for the user's exercise video along with the image for each part.

Although the present invention has been described with reference to specific embodiments and drawings, it will be appreciated that various modifications and changes can be made from the invention by those skilled in the art. For example, appropriate results may be achieved although the described techniques are performed in an order different from that described above and/or although the described components, such as a system, a structure, a device, or a circuit, are combined in a manner different from that described above and/or replaced or supplemented by other components or their equivalents.

Accordingly, other implementations, embodiments, and equivalents are within the scope of the following claims.

What is claimed is:

1. A method for assisting exercise, the method including,
providing a video providing a first video data including a first exercise movement;
obtaining a second video data including a second exercise movement obtained by responding to an input of the first video data;
extracting a fist joint information obtained by detecting plural skeleton from the second video data;
providing analysis information based on a similarity determined by comparing the first joint information with the second joint information of the first video data; and
providing a recommendation information recommends an exercise movement based on at least one of the first video data, the second video data and the analysis information from a data base including plural exercise movements, in order to recommend an appropriate exercise movement to a user.

2. A non-transitory computer-readable recording medium having recorded thereon one or more program comprising commands for executing the method of the claim 1.

* * * * *